US010514352B2

(12) United States Patent
Raghunathan et al.

(10) Patent No.: US 10,514,352 B2
(45) Date of Patent: Dec. 24, 2019

(54) HIGH DENSITY ELECTRODE ARRAYS WITH OUTLIER BEHAVIOR DETECTION CIRCUITRY AND METHODS THEREFOR

(71) Applicant: Robert Bosch GmbH, Stuttgart (DE)

(72) Inventors: Ashwin Raghunathan, San Francisco, CA (US); Sam Kavusi, Menlo Park, CA (US)

(73) Assignee: Robert Bosch GmbH, Stuttgart (DE)

( * ) Notice: Subject to any disclaimer, the term of this patent is extended or adjusted under 35 U.S.C. 154(b) by 905 days.

(21) Appl. No.: 14/986,896

(22) Filed: Jan. 4, 2016

(65) Prior Publication Data
US 2016/0216225 A1 Jul. 28, 2016

Related U.S. Application Data

(60) Provisional application No. 62/108,650, filed on Jan. 28, 2015.

(51) Int. Cl.
*G01N 27/00* (2006.01)
*G01N 27/22* (2006.01)
(Continued)

(52) U.S. Cl.
CPC ........... *G01N 27/227* (2013.01); *G01N 27/27* (2013.01); *G01R 19/16504* (2013.01); *G01R 31/00* (2013.01)

(58) Field of Classification Search
None
See application file for complete search history.

(56) References Cited

U.S. PATENT DOCUMENTS 5,592,493 A * 1/1997 Crouch .......... G01R 31/318536
324/73.1
2008/0314765 A1* 12/2008 Chibane ............. G01N 27/4163
205/775
(Continued)

OTHER PUBLICATIONS

John et al., "An automated system for rapid evaluation of high-density electrode arrays in neural prostheses; An automated system for rapid evaluation of high-density electrode arrays", Journal of Neural Engineering, Institute of Physics Publishing, Bristol, GB, vol. 8, No. 3, Apr. 15, 2011, p. 1-11.
(Continued)

Primary Examiner — Lori A. Clow
Assistant Examiner — Marie Archer
(74) Attorney, Agent, or Firm — Norton Rose Fulbright US LLP

(57) ABSTRACT

A system and method for monitoring outlier behavior in an array of n electrodes includes an electrical line, a switching circuit via which the electrodes are individually coupleable to the electrical line, a sensor; and processing circuitry, where, in each of m iterations: (i) a respective subset of electrodes is coupled by the switching circuit to the electrical line, (ii) the sensor senses an electrical parameter produced over the electrical line by the coupled subset of electrodes, and (iii) the processing circuitry obtains from the sensor a respective value of the electrical parameter, m being less than n, and the processing circuitry identifying those of the electrodes that exhibit outlier electrical behavior by finding electrical values to individually ascribe to individual ones of the electrodes of the array, which ascribed values can result in all of the respective values of all of the m iterations.

25 Claims, 12 Drawing Sheets

(51) Int. Cl.
*G01R 31/00* (2006.01)
*G01R 19/165* (2006.01)
*G01N 27/27* (2006.01)

(56) References Cited

U.S. PATENT DOCUMENTS

| | | | | |
|---|---|---|---|---|
| 2010/0301398 A1* | 12/2010 | Rothberg | ............... | G01N 27/27 257/253 |
| 2012/0300953 A1 | 11/2012 | Mauch et al. | | |
| 2014/0058239 A1* | 2/2014 | Joshi | .................... | A61B 5/0476 600/378 |
| 2014/0184383 A1* | 7/2014 | Wodnicki | ............... | G08C 19/00 340/4.3 |

OTHER PUBLICATIONS

Xu et al., "Fault Modeling and Functional Test Methods for Digital Microfluidic Biochips", IEEE Transactions on Biomedical Circuits and Systems, IEEE, US, vol. 3, No. 4, Aug. 1, 2009, pp. 241-253.
Hartinger et al., "Real-Time Management of Faulty Electrodes in Electrical Impedance Tomography", IEEE Transactions on Biomedical Engineering, IEEE Service Center, Piscataway, NJ, USA, vol. 56, No. 2, Feb. 1, 2009, pp. 369-377, XP011292695.
Al-Gayem et al., "Neural-Network Fault Diagnosis for Electrode Structures in Bio-fluidic Microsystems", Mixed-Signals, Sensors and Systems Test Workshop, 2011 IEEE 17th International, IEEE, May 16, 2011, pp. 143-148.

\* cited by examiner

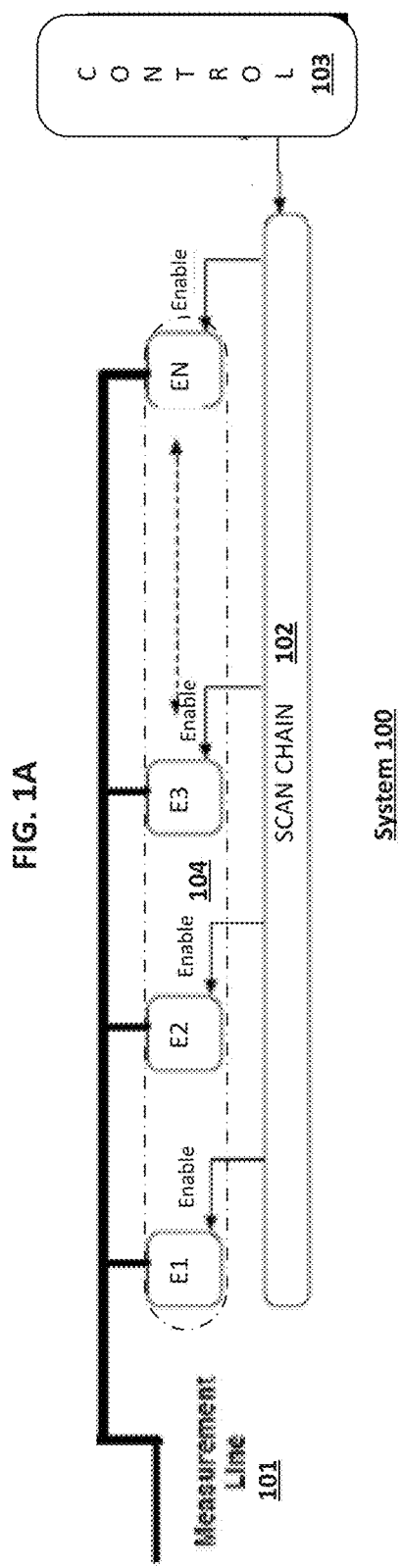

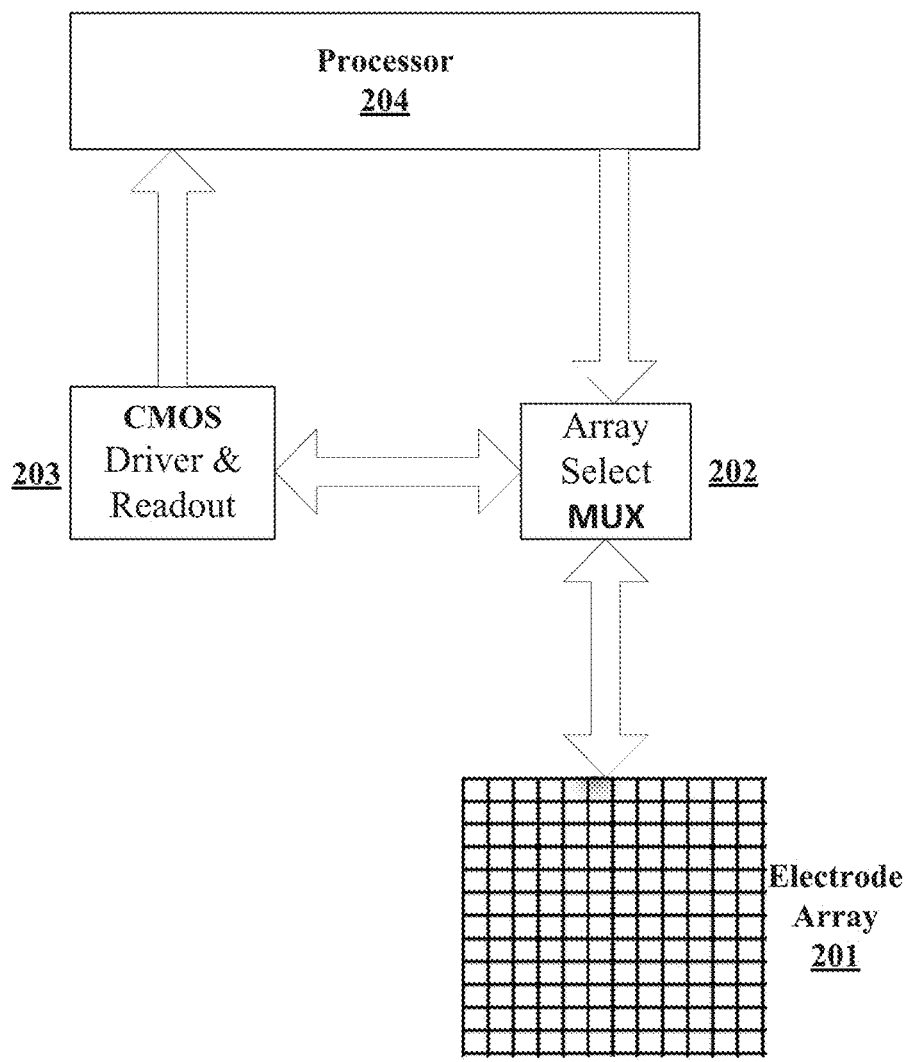

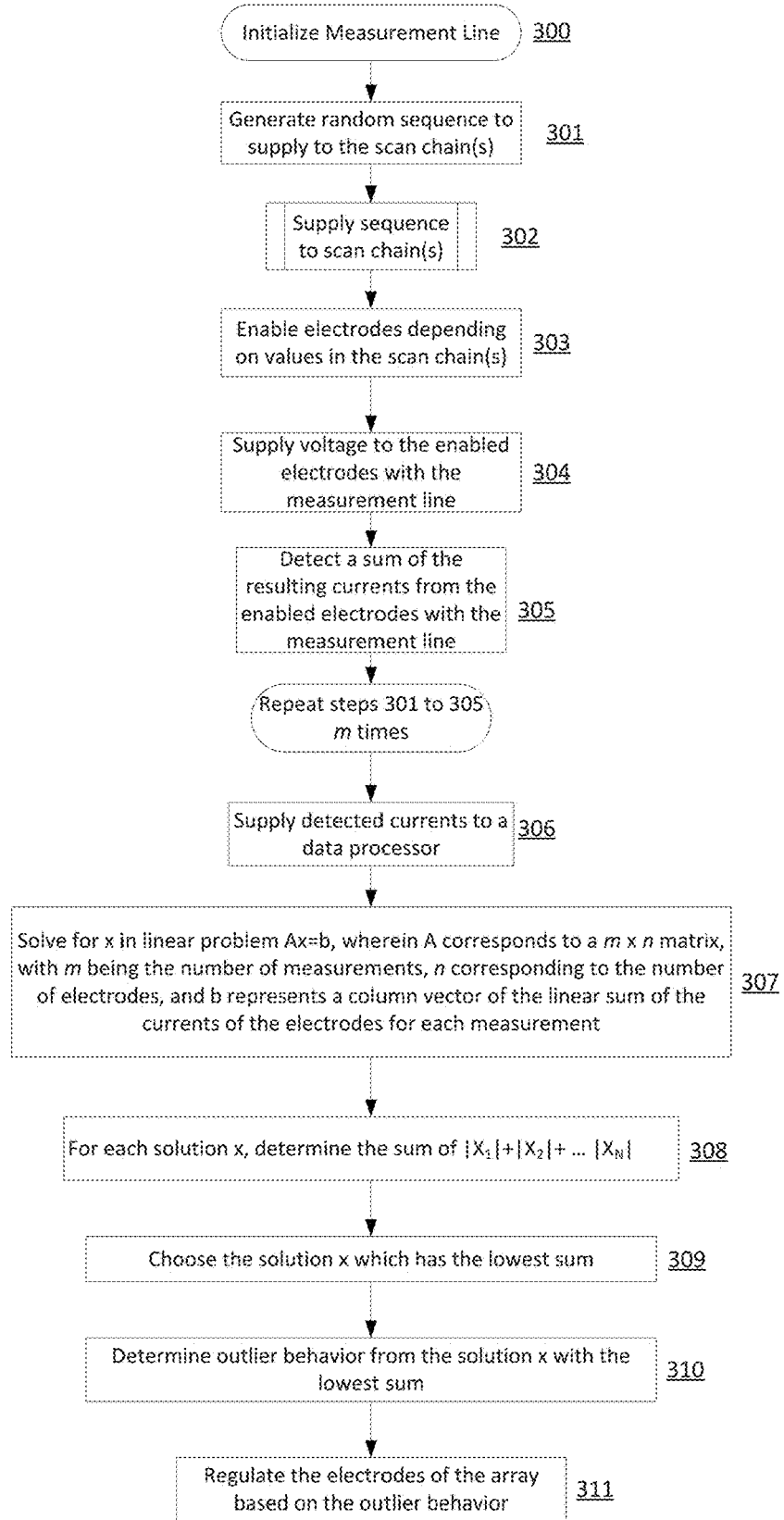

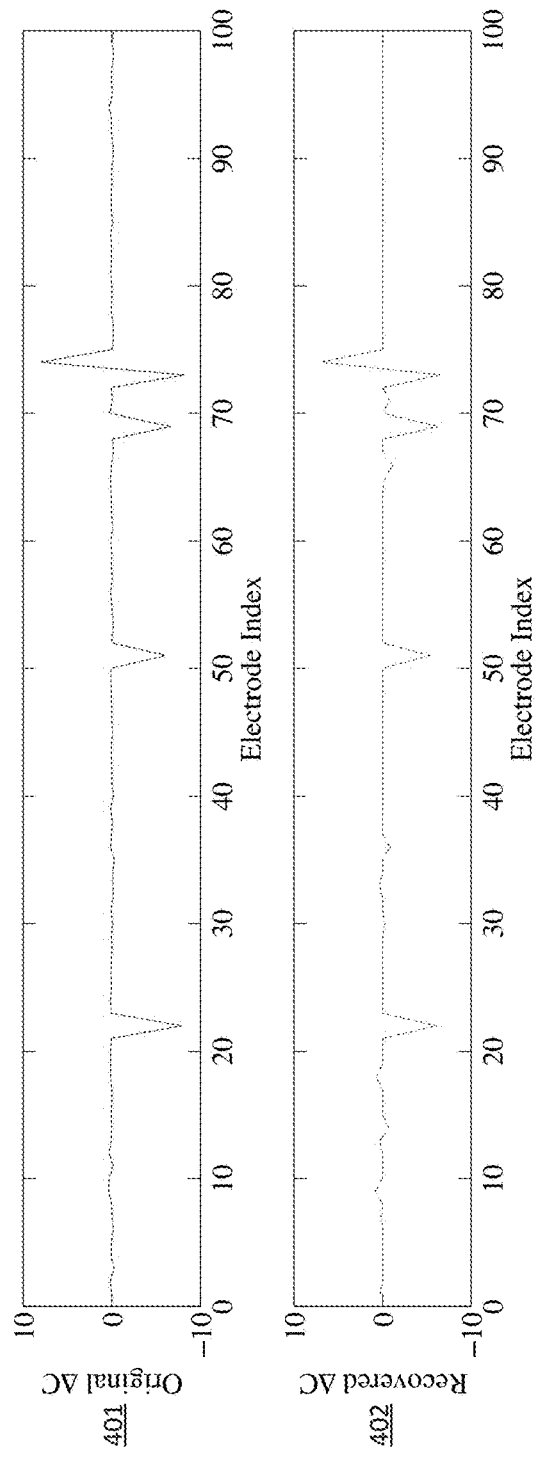

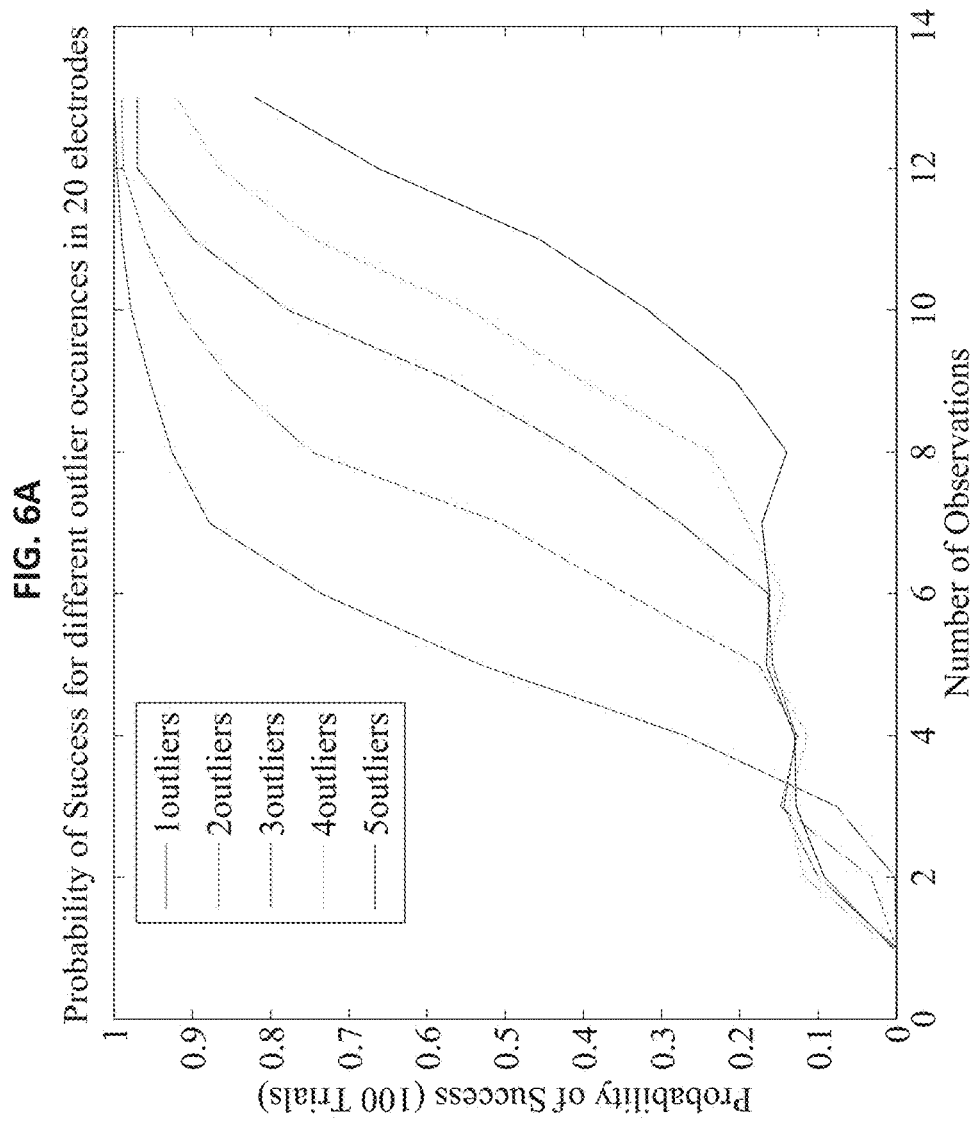

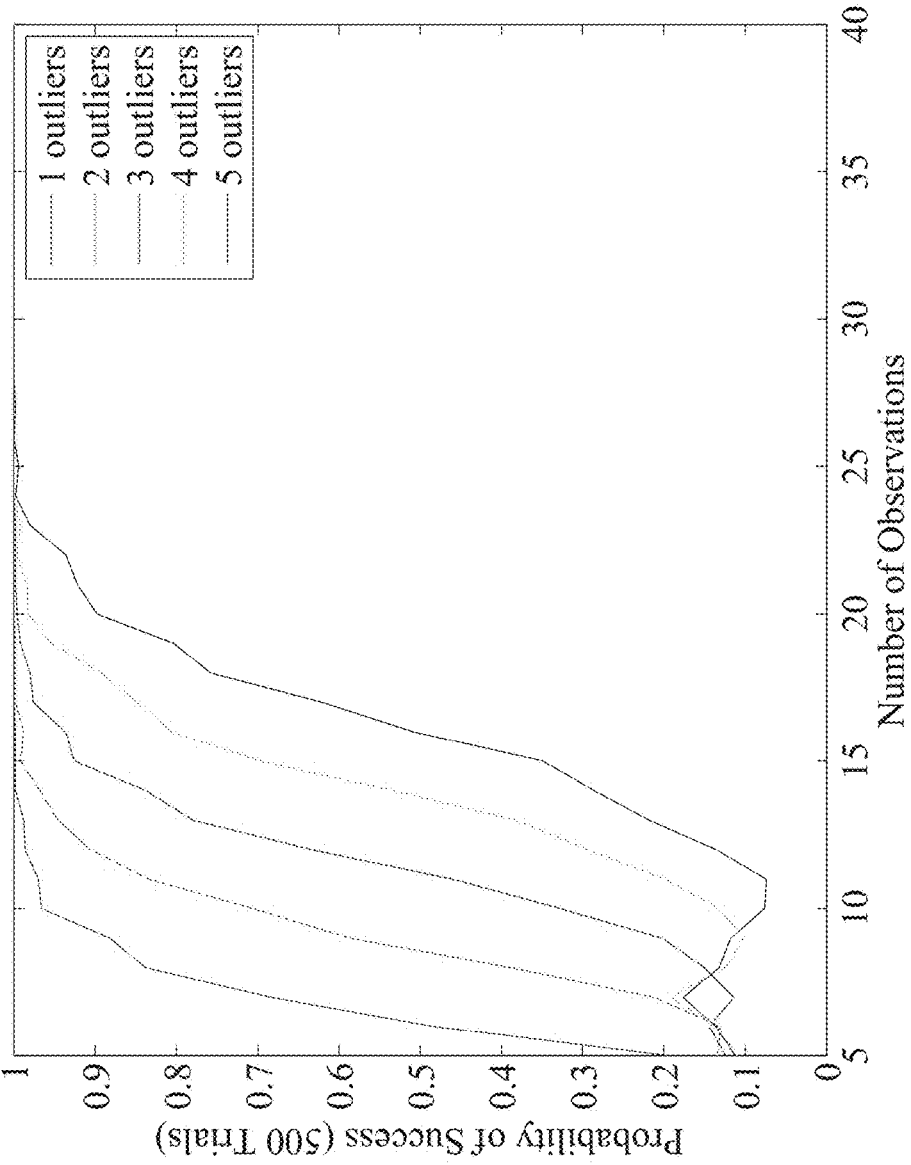

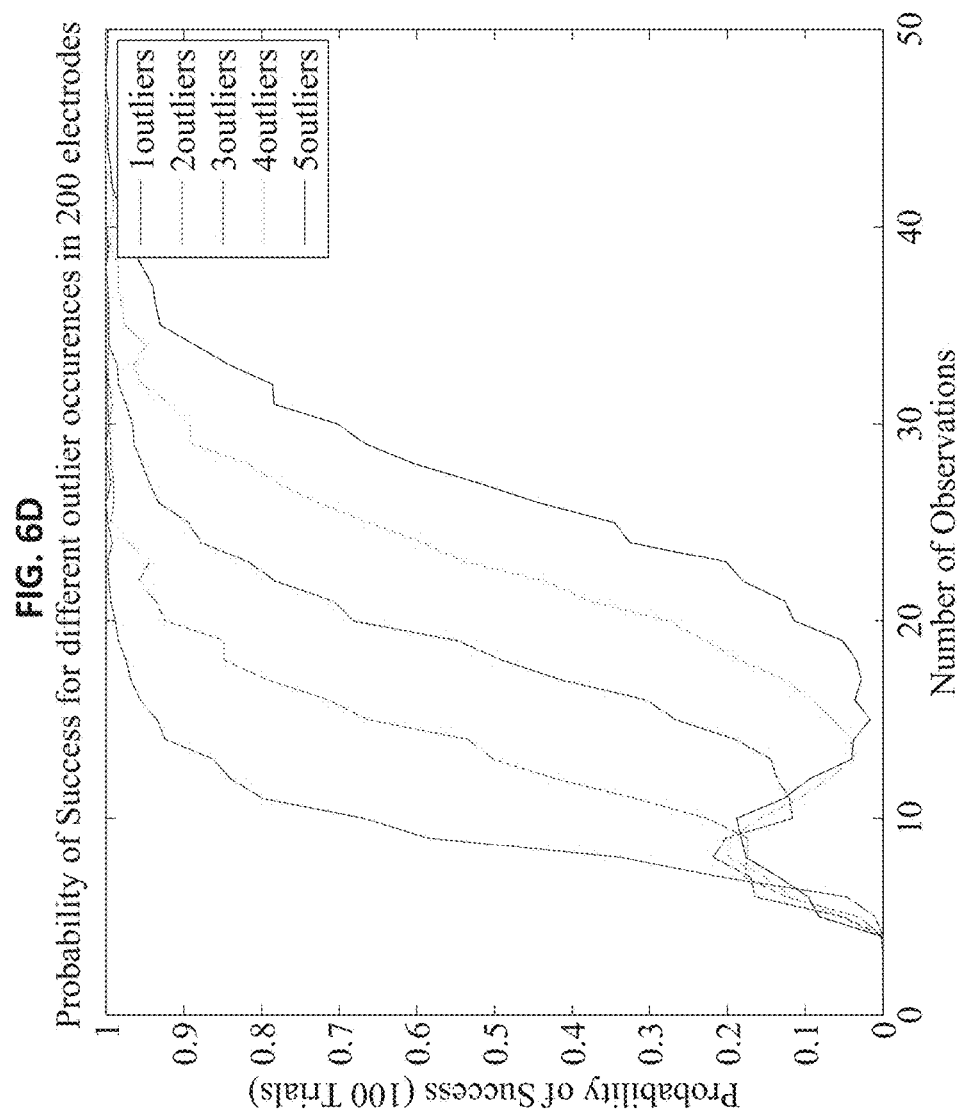

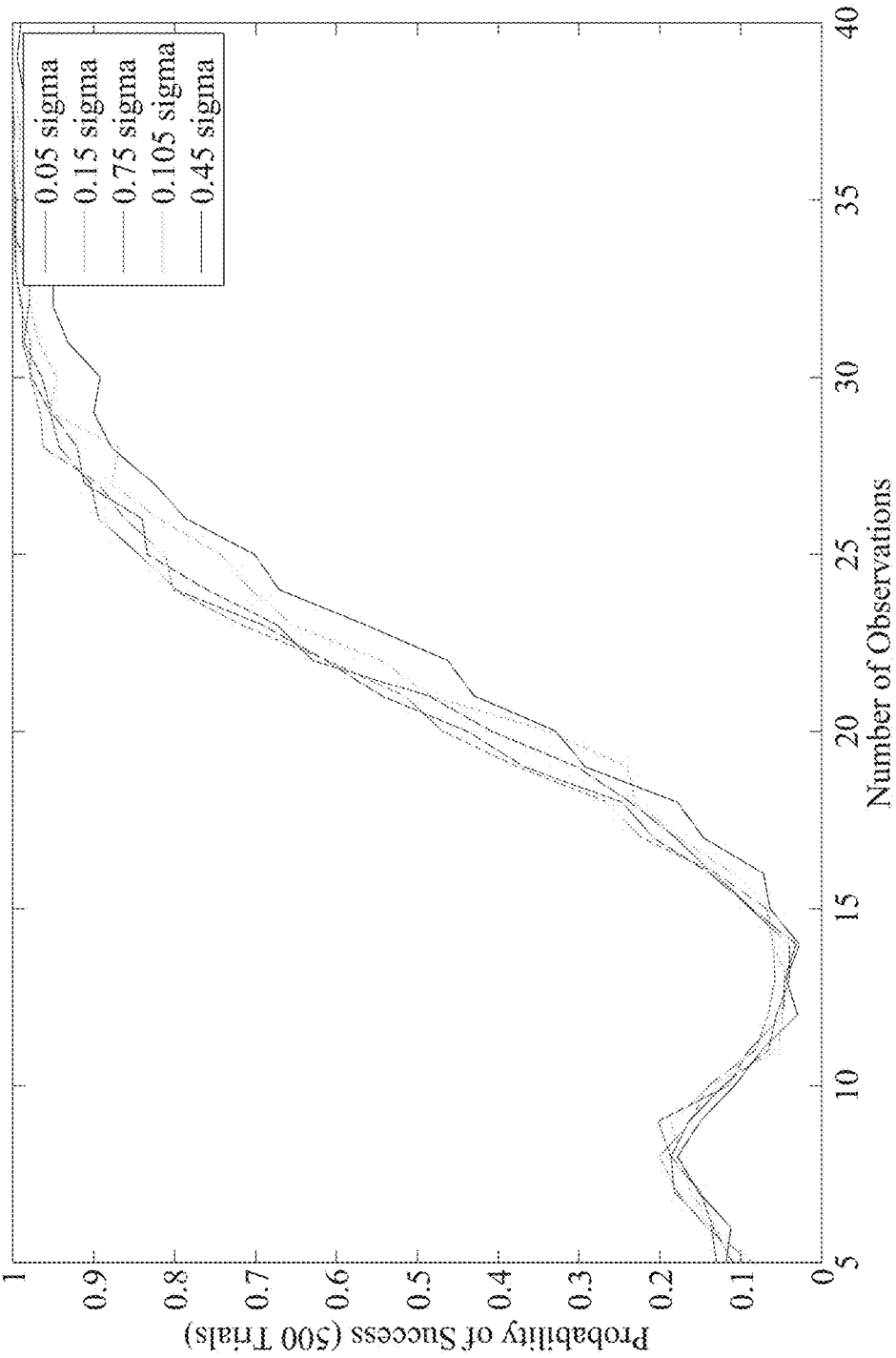

HIGH DENSITY ELECTRODE ARRAYS WITH OUTLIER BEHAVIOR DETECTION CIRCUITRY AND METHODS THEREFOR

CROSS-REFERENCE TO RELATED APPLICATION

The present application claim the benefit, under 35 U.S.C. 119(e), of U.S. Provisional Patent Application Ser. No. 62/108,650, filed Jan. 28, 2015, the entire contents of which is hereby incorporated by reference herein.

FIELD OF THE INVENTION

The present invention relates to methods and systems for efficiently detecting outlier behavior in high density electrode arrays with data processing using a reduced number of measurements.

BACKGROUND

High density electrode arrays form the backbone of many molecular sensing applications (e.g., high density electrode micro-arrays in deoxyribonucleic acid (DNA) hybridization, protein detection, etc.), and can include a platform in which a large number (e.g., several hundred/thousands) of multiplexed electrode channels are provided, which are capable of parallel operation. In the course of an experiment, a number of electrodes in a high density array can exhibit outlier behavior, which refers to any behavior that causes the current-voltage (I-V) characteristic of an electrode to significantly deviate from that of most others of the electrodes. Generally, the I-V characteristics of most of the electrodes reside within a predefined acceptable range, and an electrode is considered to significantly deviate from that of the general population of electrodes if the I-V characteristics of the electrode are more than three standard deviations from the mean of the I-V characteristics of the general population of electrodes. Similarly, an electrode can also be considered to significantly deviate if the I-V characteristics of the electrode exceed a user-defined threshold.

Such outlier behavior can be caused many factors. For example, with regard to Indium-Tin-Oxide (ITO) electrodes formed on a glass substrate, outlier behavior may be the result of tin variations causing formation of unstable hydrogel on the surface of the electrode. Generally, the surface of the ITO electrode is composed of different species with dynamically varying concentrations, which are responsible for electrochemical "hot-spots" (e.g., a lot of activity) and "dead-zones" (e.g., very little or no activity). The outlier behavior can also be dynamic in nature, where an electrode exhibits outlier behavior for some portion of the experiment and functions normally during another portion of the experiment.

Methods to determine outlier behavior in electrodes include either (1) periodically testing each electrode on an individual basis during the course of an experiment or (2) re-validating any data points that significantly deviated from expected values to rule out outlier behavior as the cause of the deviation.

Generally, the first option is useful for (a) low density electrode arrays (i.e., an array with a small number of electrodes) or (b) high density electrode arrays with a single faulty electrode. With regard to low density electrode arrays, assuming that a typical electrochemical measurement takes about six seconds, each electrode of the array can be tested on an individual basis (i.e., encompassing one measurement) in a relatively short period of time. In other words, during each measurement, a voltage is applied to a single electrode and the current drawn from that electrode is compared to an expected value to determine if it is an outlier. To detect a single faulty electrode among an electrode array with 'N' electrodes of a high density electrode array, $\log_2 N$ measurements would need to be performed. In other words, for the first measurement, a voltage is applied to two subsets (with each subset containing N/2 electrodes) of the N electrodes and the linear sums of the currents drawn from each of the subsets are compared to an expected current value for each of the subsets. Therefore, if a current sum of one of the subsets deviates from an expected current value, then it can be assumed that the subset contains the outlier. Thus, in order to determine which electrode is the outlier, the above process (i.e., splitting the array of electrodes into two equal subsets during the measurement) is repeated for each subset indicated as including an outlier in a prior iteration. For example, to detect one electrode among a 4096-element array, it would take $\log_2(4096)$ or 12 measurements. Therefore, assuming that each measurement takes six seconds to perform, determining the single outlier among the 4096 element array would take around 72 seconds.

However, as the number of outlier electrodes increase, the number of measurements required to identify them (i.e., with a high level of confidence) approaches the total number of electrodes. In general, in order to determine more than 1 outlier in an N element array, the number of required measurements rapidly approaches N, requiring almost all of the electrodes to be individually monitored. This is because outlier behavior occurs in both the positive and negative direction and, therefore, merely summing the currents of a subset of electrodes may not show any significant deviation from an expected current value for the subset. Accordingly, applying the $\log_2 N$ approach would prove futile. Therefore, to determine more than 1 outlier in a 4096-element array, it would take nearly 4096 measurements, which translates to nearly seven hours of measurement time (assuming that each measurement takes six seconds to perform). Moreover, the above-mentioned outlier monitoring may need to be performed several times during the course of an experiment due to the dynamic nature of the underlying phenomena.

Further, the second option (i.e., re-validating any data points that significantly deviate from expected values to rule out outlier behavior as the cause of the deviation) is not very attractive because, in many cases, it would require the repetition of an entire experiment, which might not be practical due to a variety of reasons including, but not limited to, additional cost, limited quantity of samples.

SUMMARY

Example embodiments of the present invention provide a system including an electrode array, and circuitry and an associated method for efficiently detecting outlier behavior in the electrode array using a reduced number of measurements, such that outliers in an N-element array are detected using much fewer than N measurements.

According to an example embodiment of the present invention, a system includes an array of n electrodes; an electrical line; a switching circuit via which the electrodes are individually coupleable to the electrical line; a sensor; and processing circuitry, the system being configured for the following to be performed in each of m iterations: (i) coupling, by the switching circuit, a respective subset of electrodes to the electrical line; (ii) sensing, by the sensor, an electrical parameter produced over the electrical line by the coupled subset of electrodes; and (iii) obtaining, by the processing circuitry and from the sensor, a respective value of the electrical parameter, where m is less than n, and the processing circuitry is configured to identify those of the electrodes that exhibit outlier electrical behavior by finding electrical values to individually ascribe to individual ones of the electrodes of the array, which ascribed values can result in all of the respective values of all of the m iterations.

In an example embodiment, the subset of electrodes being coupled differs between at least two of the iterations.

In an example embodiment, the processing circuitry is configured to determine a plurality of sets of electrical values that can be ascribed to the individual electrodes and that each can result in the all of the respective values of all of the m iterations, and is further configured to subsequently select from the plurality of sets, the set whose sum is the least of all respective sums of the respective sets.

In an example embodiment, the processing circuitry is configured to calculate $$\begin{pmatrix} a_{11} & a_{12} & \ldots & \ldots & a_{1n} \\ a_{21} & a_{22} & \ldots & \ldots & a_{2n} \\ \vdots & \vdots & \ldots & \vdots & \vdots \\ a_{m1} & a_{m2} & \ldots & \ldots & a_{mn} \end{pmatrix} \begin{pmatrix} x_1 \\ x_2 \\ \vdots \\ x_n \end{pmatrix} = \begin{pmatrix} b_1 \\ b_2 \\ \vdots \\ m \end{pmatrix},$$

each row of $$\begin{pmatrix} a_{11} & a_{12} & \ldots & \ldots & a_{1n} \\ a_{21} & a_{22} & \ldots & \ldots & a_{2n} \\ \vdots & \vdots & \ldots & \vdots & \vdots \\ a_{m1} & a_{m2} & \ldots & \ldots & a_{mn} \end{pmatrix}$$

and of $$\begin{pmatrix} b_1 \\ b_2 \\ \vdots \\ m \end{pmatrix}$$

corresponds to a respective one of the iterations, each column of $$\begin{pmatrix} a_{11} & a_{12} & \ldots & \ldots & a_{1n} \\ a_{21} & a_{22} & \ldots & \ldots & a_{2n} \\ \vdots & \vdots & \ldots & \vdots & \vdots \\ a_{m1} & a_{m2} & \ldots & \ldots & a_{mn} \end{pmatrix}$$

corresponds to a respective one of the electrodes in the array, each position of $$\begin{pmatrix} a_{11} & a_{12} & \ldots & \ldots & a_{1n} \\ a_{21} & a_{22} & \ldots & \ldots & a_{2n} \\ \vdots & \vdots & \ldots & \vdots & \vdots \\ a_{m1} & a_{m2} & \ldots & \ldots & a_{mn} \end{pmatrix}$$

is populated with either a first value or a second value depending on whether the respective electrode was enabled or disabled in the respective iteration, each position of $$\begin{pmatrix} b_1 \\ b_2 \\ \vdots \\ m \end{pmatrix}$$

is populated with the respective value of the electrical parameter for the respective iteration, and each of the x values is an unknown, which the processing circuitry determines by finding the set of x values that satisfy $$\begin{pmatrix} a_{11} & a_{12} & \ldots & \ldots & a_{1n} \\ a_{21} & a_{22} & \ldots & \ldots & a_{2n} \\ \vdots & \vdots & \ldots & \vdots & \vdots \\ a_{m1} & a_{m2} & \ldots & \ldots & a_{mn} \end{pmatrix} \begin{pmatrix} x_1 \\ x_2 \\ \vdots \\ x_n \end{pmatrix} = \begin{pmatrix} b_1 \\ b_2 \\ \vdots \\ m \end{pmatrix}.$$

In an example embodiment, the processing circuitry is configured to determine a plurality of sets of x values that are each plausible, sum each set of x values, and select the set whose sum is smallest.

In an example embodiment, each x value represents a contribution of a respective one of the electrodes towards the values of the sensed electrical parameters produced over the electrical line during the iterations.

According to an example embodiment of the present invention, a system for monitoring and regulating an electrode array includes a measuring circuit that is configured to perform measurements in which the measuring circuit supplies voltages to enabled electrodes in the electrode array and detects current across the enabled electrodes in the electrode array, the system further includes at least one scan chain, each memory element of which corresponds to an electrode in the electrode array, and the system further includes a processing circuit configured to, in a first step, generate a random sequence of 1s and 0s, where the sequence corresponds to a number of electrodes in the electrode array, in another step, supply the random sequence to the at least one scan chain, in another step, solve for a column vector x in Ax=b, where: A corresponds to a m×n matrix populated with the 1s and 0s of the random sequence; m is a number of predefined measurements and n corresponds to the number of electrodes in the electrode array; and b represents a column vector corresponding to the sum of the resulting currents of the electrodes for each of the measurements. In another step, the processing circuit is configured to determine for each solution x, a sum of $|X_1|+|X_2|+ \ldots |X_N|$, where $|X_1|, |X_2| \ldots |X_N|$ correspond to elements of the column vector x. In another step, the processing circuit is configured to select a solution x which has the lowest sum of $|X_1|+|X_2|+ \ldots |X_N|$ and determine at least one faulty electrode from the solution x with the lowest sum. In example embodiment, the processing circuit is configured to regulate the electrodes of the electrode array based on the at least one determined faulty electrode.

In an example embodiment, the electrode array is implemented in (1) a glass slide or (2) a complementary metal-oxide semiconductor (CMOS) chip.

In an example embodiment, the electrode array is implemented on a combination of a glass slide and a complementary metal-oxide semiconductor (CMOS) chip.

In an example embodiment, the at least one scan chain includes a shift register.

In an example embodiment, the measuring circuit and the at least one scan chain interface with the electrodes of the electrode array through at least one of a (1) decoder circuit and (2) multiplexer.

In an example embodiment, the scan chain is implemented with (1) capacitors or (2) flip-flops.

According to an example embodiment of the present invention, a method for monitoring and regulating an electrode array includes a processor generating a random sequence of 1s and 0s, where the sequence corresponds to a number of electrodes in the electrode array; the processor supplying the random sequence to at least one scan chain; enabling the electrodes in the electrode array depending on values in the at least one scan chain; supplying a voltage to the enabled electrodes via a measurement line; detecting a sum of the resulting currents across the enabled electrodes; repeating the previous steps a pre-defined number of times; supplying the detected currents to the processor; solving, by the processor, for a column vector x in Ax=b, where A corresponds to a m×n matrix populated with the 1s and 0s of the random sequence, m is a number of predefined measurements, n corresponds to the number of electrodes in the electrode array, and b represents a column vector corresponding to the sum of the resulting currents of the electrodes for each of the measurements. For each solution x, the processor determines a sum of $|X_1|+|X_2|+ \ldots |X_N|$, where $|X_1|, |X_2| \ldots |X_N|$ correspond to elements of the column vector x. The processor selects a solution x which has the lowest sum of $|X_1|+|X_2|+ \ldots |X_N|$, determines at least one faulty electrode from the solution x with the lowest sum, and regulates the electrodes of the electrode array based on the at least one determined faulty electrode.

In an example embodiment, the regulating includes (1) adjusting the voltage being applied to the faulty electrode or (2) disabling the faulty electrode.

In an example embodiment, the method further includes dividing, by the processor, the electrode array into at least two sub-arrays, determining, by the processor, which sub-array of the at least two sub-arrays includes the at least one faulty electrode, and reapplying the detection method to the sub-array determined as including the at least one faulty electrode.

In an example embodiment, the at least one faulty electrode is determined from non-zero elements of the solution x with the lowest sum.

In an example embodiment, m<n.

In an example embodiment, the random sequence of 1s and 0s is supplied to at least two scan chains, and the random sequence supplied to the first scan chain is different than the random sequence supplied to at least one second scan chain.

In an example embodiment, current-voltage characteristics of the at least one faulty electrode significantly deviate from a mean of the current-voltage characteristics of a general population of electrodes in the electrode array.

Example embodiments of the present invention are directed to a non-transitory computer readable medium containing program instructions for detecting outlier behavior in an electrode array using a reduced number of measurements, where execution of the program instructions by one or more processors of a computer system causes the one or more processors to carry out the steps of one or more of the methods described herein.

BRIEF DESCRIPTION OF THE DRAWINGS

FIG. 1A depicts a system to detect outlier behavior of an array, according to an example embodiment of the present invention.

FIG. 2 is a block diagram of a system to detect outlier behavior, according to an example embodiment of the present invention.

FIG. 3 is a flowchart that illustrates a method to detect outlier behavior, according to an example embodiment of the present invention.

FIG. 4 depicts (1) a graph of example actual outlier behavior and (2) a graph of corresponding results from the outlier detection method, according to an example embodiment of the present invention.

FIG. 6A depicts the probability of success for different outlier occurrences in 20 electrodes using the simulation method of FIG. 5 for 100 trials, according to an example embodiment of the present invention.

FIG. 6B depicts the probability of success for different outlier occurrences in 50 electrodes using the simulation method of FIG. 5 for 500 trials, according to an example embodiment of the present invention.

FIG. 6D depicts the probability of success for different outlier occurrences in 200 electrodes using the simulation method of FIG. 5 for 100 trials, according to an example embodiment of the present invention.

FIG. 6E depicts the probability of success for different measurement noise variances for 5 outliers in 100 electrodes using the simulation method of FIG. 5 for 500 trials, according to an example embodiment of the present invention.

DETAILED DESCRIPTION

FIG. 1A illustrates a system including an electrode array, with circuitry utilized to detect outlier behavior in the electrodes of the array. System 100 includes a measurement line 101, scan chain 102, control 103 and electrodes 104. In an example embodiment, control 103 is configured to generate sequences of 1s and 0s, e.g., random sequences thereof, to supply to the scan chain 102, where the sequences each identify which of the electrodes are to be enabled and which of the electrodes are to be disabled during a test, and where the measurement line 101 is able to supply a voltage to, and detect a current across, only the enabled ones of the electrodes. In an example embodiment, an electrode is enabled if a high level ("1") is supplied to the electrode from the scan chain 102, and an electrode is disabled if a low level ("0") is supplied to the electrode 102. In an example embodiment, the scan chain 102 is a shift register, where each memory element of the shift register corresponds to a respective one of the electrodes of the electrode array. In an example embodiment, the scan chain 102 sets the plurality of electrodes in the electrode array simultaneously to their respective enabled and disabled statuses. In an example embodiment, the measurement line 101 supplies a voltage to all of the enabled electrodes simultaneously, for detection of the current across the enabled electrodes.

Figure 1B:
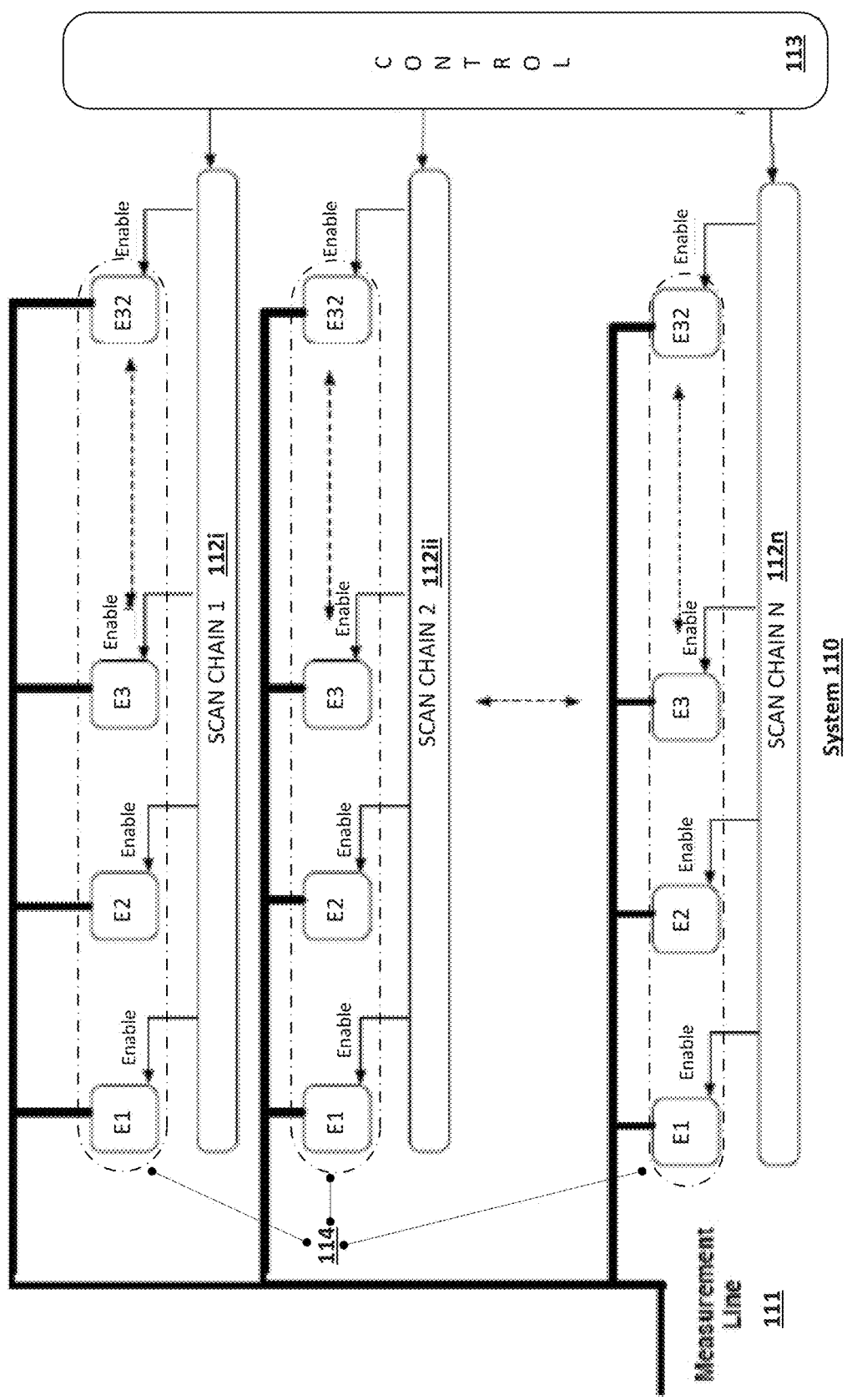
FIG. 1B depicts a system to detect outlier behavior of an array, where the array elements are arranged in rows, according to an example embodiment of the present invention.

FIG. 1B depicts another example embodiment of a system utilized to detect outlier behavior. The system of FIG. 1B is similar to that of FIG. 1A, except that the electrodes are divided into sections, e.g., by row, with respective scan chains (112i-112n) and measurement line 111 branches being provided to the physical respective groups of the electrode array. For example, in system 110, each row of the electrode array contains 32 electrodes, and control 113 supplies, for each test of the array, respective, random sequences of 1s and 0s to scan chains 112i to 112n for enabling and disabling different electrodes in the respective rows of the electrode array. Similar to system 100, the branches of measurement line 111 simultaneously supply a voltage to, and detect a current across, all of the electrodes of the array, which have been enabled by their respective scan chains 112i-112n.

In an example embodiment of the present invention, the system includes circuitry configured to process electrical signals sensed from the measurement line 111 in response to the voltage supply to the enabled electrodes, to detect those of the electrodes that exhibit outlier behavior. In an example embodiment, the circuitry includes a sensor to obtain the signal, the sensor being coupled to a processor for supplying data representing the sensed signal to the processor. For example, in an example embodiment, the sensor senses an analog signal, which is fed to an analog-to-digital converter to produce a corresponding digital signal, which is provided to the processor. The processor can be implemented using any appropriate processing circuit and device or combination thereof, e.g., a Central Processing Unit (CPU) of a Personal Computer (PC) or other workstation processor, to execute code provided, e.g., on a non-transitory hardware computer-readable medium including any conventional memory device, to perform any of the methods described herein, alone or in combination. The memory device can include any suitable permanent and/or temporary memory circuits or combination thereof, a non-exhaustive list of which includes Random Access Memory (RAM), Read Only Memory (ROM), Compact Disks (CD), Digital Versatile Disk (DVD), flash memory and magnetic tape.

In an example embodiment, the system is configured to iteratively set different respective sets of the electrodes of the array to enabled status, taking a respective measurement in each such iteration, and supplying the respective sensed signal to the processor. In an example embodiment, the processor is configured to then identify the outlier electrodes based on the combination of signal values obtained over a plurality of the iterations, using the equation of Ax=b, where 'A' is a m×n matrix, with m being the number of measurements (iterations), n corresponding to the number of electrodes in the array, 'x' is a n×1 matrix corresponding to the unknown individual current values of the respective electrodes, and 'b' is a m×1 matrix of the respective sum of the currents of all of the enabled electrodes of each measurement iteration. In an example embodiment, m (i.e., the number of measurements) is predefined.

It is possible for a number of combinations of values to be pluggable into the 'x' matrix and satisfy the relationship Ax=b. In an example embodiment, the processor determines which of the possible combinations of values that are pluggable into the 'x' matrix, when added together produces the lowest sum. The processor then determines which of that determined value combination is/are a statistical outlier and identifies the corresponding electrode(s) as the outlier electrode(s).

For example, in an example embodiment, for each solution x to Ax=b, the processor calculates the sum of $|x_1|+|x_2|+ \ldots |x_N|$, and then selects the outliers from a solution x which has the lowest sum of $|x_1|+|x_2|+ \ldots |x_N|$. For example, if the electrochemical quantity of interest (i.e., I-V characteristic) is a deviation in electrode double layer capacitance from the average values (i.e., $\Delta C$), in an example embodiment, it is assumed that most of the $\Delta C$'s are very close to zero, and the outliers are determined by solving for $\Delta C$ in the linear problem, $A(\Delta C)=b$. In order to determine $\Delta C_1, \Delta C_2, \Delta C_3 \ldots \Delta C_N$, the linear problem is expanded to $a_{11}\Delta C_1+a_{12}\Delta C_2+a_{13}\Delta C_3 \ldots +a_{1N}\Delta C_N=b_1$, where $a_{11}, a_{12}, a_{13} \ldots a_{1N}$ represent the electrodes of the array and are randomly chosen to be either 0 or 1 in each of m<<n iterations, where, for example, a 0 is set for each electrode that is disabled in the respective iteration and a 1 is set for each electrode that is enabled in the respective iteration, to get:

$$\begin{pmatrix} a_{11} & a_{12} & \ldots & \ldots & a_{1n} \\ a_{21} & a_{22} & \ldots & \ldots & a_{2n} \\ \vdots & \vdots & \ldots & \vdots & \vdots \\ a_{m1} & a_{m2} & \ldots & \ldots & a_{mn} \end{pmatrix} \begin{pmatrix} \Delta C_1 \\ \Delta C_2 \\ \vdots \\ \Delta C_n \end{pmatrix} = \begin{pmatrix} b_1 \\ b_2 \\ \vdots \\ b_m \end{pmatrix}.$$

For example, if electrodes 1 and n are enabled and electrode 2 is disabled in iteration 1, electrodes 2 and n are enabled and electrode 1 is disabled in iteration 2, and electrode 2 is enabled and electrodes 1 and n are disabled in iteration n, then matrix A would include the following values:

$$\begin{pmatrix} 1 & 0 & \ldots & \ldots & 1 \\ 0 & 1 & \ldots & \ldots & 1 \\ \vdots & \vdots & \ldots & \ldots & \vdots \\ 0 & 1 & \ldots & \ldots & 0 \end{pmatrix}$$

In each iteration, the measurement line 101/111 obtains a value for an electrical parameter formed by the combination of electrical responses of all enabled electrodes of the iteration. Those values populate matrix b, such that the sensed value of iteration 1 populates $b_1$, the sensed value of iteration 2 populates $b_2$, the sensed value of iteration n populates $b_n$, etc.

Then, for each solution of a set of values for $\Delta C_1, \Delta C_2, \Delta C_3 \ldots \Delta C_N$ that satisfies the above equation, a sum $|\Delta C_1|+|\Delta C_2|+ \ldots |\Delta C_N|$ is determined, and the outliers are selected from the solution $\Delta C_1, \Delta C_2, \Delta C_3 \ldots \Delta C_N$ with the lowest sum $|\Delta C_1|+|\Delta C_2|+ \ldots |\Delta C_N|$. In an example embodiment, other parameters of interest can be obtained in similar fashion including, but not limited to, exchanged current density at a particular element, polarization conductances, etc.

Although only less than n iterations are performed, the outliers can be determined because the I-V characteristics of the general population of electrodes in a high density electrode array generally show strong clustering, with only a few outliers. A well-designed electrode array with only a few of the electrodes exhibiting a significant deviation in I-V characteristics, i.e., a sparse distribution of the outliers compared to the general population of electrodes, can be assumed, and, according to compressed sensing theory, N unknowns can be determined from less than N measurements with high probability if most of the N unknowns of interest are zero (i.e., the N-unknowns are sparse). Furthermore, particularly because of the sparseness of outliers, in an example embodiment, as noted above, x is chosen such that the linear equation is satisfied and the $l_1$-norm ($|x_1|+|x_2|+\ldots|x_N|$) is minimized. In other words, an x is chosen such that a fewest number of non-zero elements satisfies the equation, and the outliers in the high density electrode array are selected from the non-zero elements of x.

FIG. 2 is a block diagram of a system utilized to detect outlier behavior, according to an example embodiment of the present invention. The illustrated system includes an electrode array 201, an array select arrangement 202, a driver and readout arrangement 203 and a processor 204. In an example embodiment, the processor 204 is configured to generate and provide a random sequence of 1s and 0s for selecting which of the electrodes of the array are enabled in a test iteration and which of the electrodes of the array are disabled in the test iteration, like the functionality described above for controls 103 and 113 of FIGS. 1A and 1B. The random sequences of 1s and 0s correspond to and populate the coefficients $a_{11}$ to $a_{mn}$ in the above-described matrix A of Ax=b.

Thus, processor 204 generates the matrix determining which electrodes in the electrode array will be measured. In an example embodiment, the processor 204 also determines (1) the solution(s) for x in Ax=b and (2) which of the possible solutions has the lowest sum of $|x_1|+|x_2|+\ldots|x_N|$. In an example embodiment, the processor 204 performs compressed sampling including the minimization of the $l_1$-norm ($|x_1|+|x_2|+\ldots|x_N|$) to find the solution.

Array select arrangement 202 is configured to control the switching of the electrodes of the array 201, to connect the processor 204 and the driver and readout arrangement 203 to the electrodes of the electrode array 201 that have been selected by the processor 204. In an example embodiment, the array select 202 includes a multiplexer (MUX) for accessing groups of electrodes. In an example embodiment, the device includes a circuit via which the processer 204 and the driver and readout arrangement 203 interface with the electrodes in electrode array 201.

In an example embodiment, the driver and readout arrangement 203 is configured to obtain the measurement of the electrical response of the electrodes in electrode array 201. For example, the driver and readout arrangement 203 includes measure lines 101/111 of FIGS. 1A and 1B and supplies voltage to, and detects current through, the enabled electrodes in electrode array 201. In an example embodiment, the driver and readout arrangement 203 includes a complementary metal-oxide semiconductor ("CMOS") to sense the electrical measurements. In an example embodiment, the driver and readout arrangement 203 transmits, e.g., a digital form of, the resulting detected currents from electrode array 201 to processor 204 after m measurements, or, alternatively, respective measurements after respective ones of the m measurements.

As noted above, in an example embodiment, the sum of the currents detected during each measurement correspond to column vector b in Ax=b. For example, $b_1$ corresponds to the sum of the currents detected at the enabled electrodes during the first measurement. Accordingly, with matrix A and column vector b, the processor 204 is configured to solve for the x matrix that satisfies Ax=b and minimizes the sum $|x_1|+|x_2|+\ldots|x_N|$, and recover the variables in column vector x corresponding to the outliers in the electrode array 201.

In an example embodiment, the electrode array 201 is implemented on a glass slide. In an alternative example embodiment, the electrode array 201 is implemented on a CMOS chip. In an alternative example embodiment, the system includes a combination of a glass slide and a CMOS chip. For example, in an example embodiment, the glass slide is utilized to implement the electrode array and decoder functions while the CMOS chip is implemented to contain all of the post-processing and data acquisition circuits. Further, in an alternative example embodiment, the entire system (i.e., the electrode array, the decoder, and the data acquisition blocks) is implemented in a CMOS platform.

In an example embodiment, the scan chains are implemented with capacitors. In an alternative example embodiment, the scan chains are implemented with flip flops.

FIG. 3 illustrates an example method to monitor and regulate electrodes of an electrode array. In step 300, the measurement line (e.g., 101/111) is initialized. Then, in step 301, a processor/controller (e.g., 204/103/113) generates a random sequence of 0s and 1s to supply to a scan chain(s) (e.g., scan chains 102, 112$i$-112$n$). In step 302, the generated random sequence is supplied to the scan chain(s). In step 303, selected ones of the electrodes in the electrode array are enabled depending on the values in each memory element of the scan chain corresponding to the electrode. In step 304, the measurement line supplies a voltage to the enabled electrodes. Then, in step 305, the measurement line detects a sum of the currents across the enabled electrodes. In an example embodiment, steps 301-305 are repeated m times. In step 306, the detected currents of the m measurements are supplied to a data processor (e.g., processor 204). In step 307, the data processor solves for x in Ax=b, where A corresponds to a m×n matrix, with m being the number of measurements, n corresponding to the number of electrodes, and b represents a column vector of the linear sums of the currents of the electrodes for the respective m measurements. Then, in step 308, for each solution x, the sum of $|x_1|+|x_2|+|x_N|$ is determined. In step 309, the solution with the lowest sum is chosen. In step 310, the outliers in the electrode array are determined from the solution x selected in step 309. In step 311, the electrodes in the electrode array are regulated based on the outlier behavior determined in step 310, for example, by adjusting the voltage being applied to the faulty electrode or disabling the electrode completely. In an example embodiment, a processor (e.g., processor 204) performs the regulation of the electrodes via the measure line.

In an example embodiment, after determining the outliers of the electrode array with the outlier detection method of FIG. 3, the detection method is reapplied on only the group of faulty electrodes, in order to further refine the I-V characteristic values of the detected faulty electrodes. For example, the re-performance of the method can be done a predetermined number of times. Alternatively, the system is configured to receive user input setting the number of times to re-perform the method.

In an alternative example embodiment, sub-arrays within the electrode array are predefined, and the method is reapplied to only those predefined sub-arrays that include at least one electrode identified in the prior performance of the method as being faulty.

FIG. 4 shows (1) a graph 401 of example actual outlier behavior of the electrode array and (2) a graph 402 of example results from the outlier detection method regarding the behavior of the electrodes, corresponding to the actual outlier behavior of the graph 401. As demonstrated by graphs 401 and 402, the electrode array to which the graphs correspond include 100 electrodes and the electrochemical quantity of interest is the deviation in electrode double layer capacitance from the average values (i.e., ΔC). Further, as depicted in graph 401, most of the ACs of the electrode array are very close to zero (e.g., making the electrode array a perfect candidate for the detection method of the present invention). Further, as depicted in graph 402, the detection method of the present invention successfully detected the most deviating ΔCs.

Figure 5:
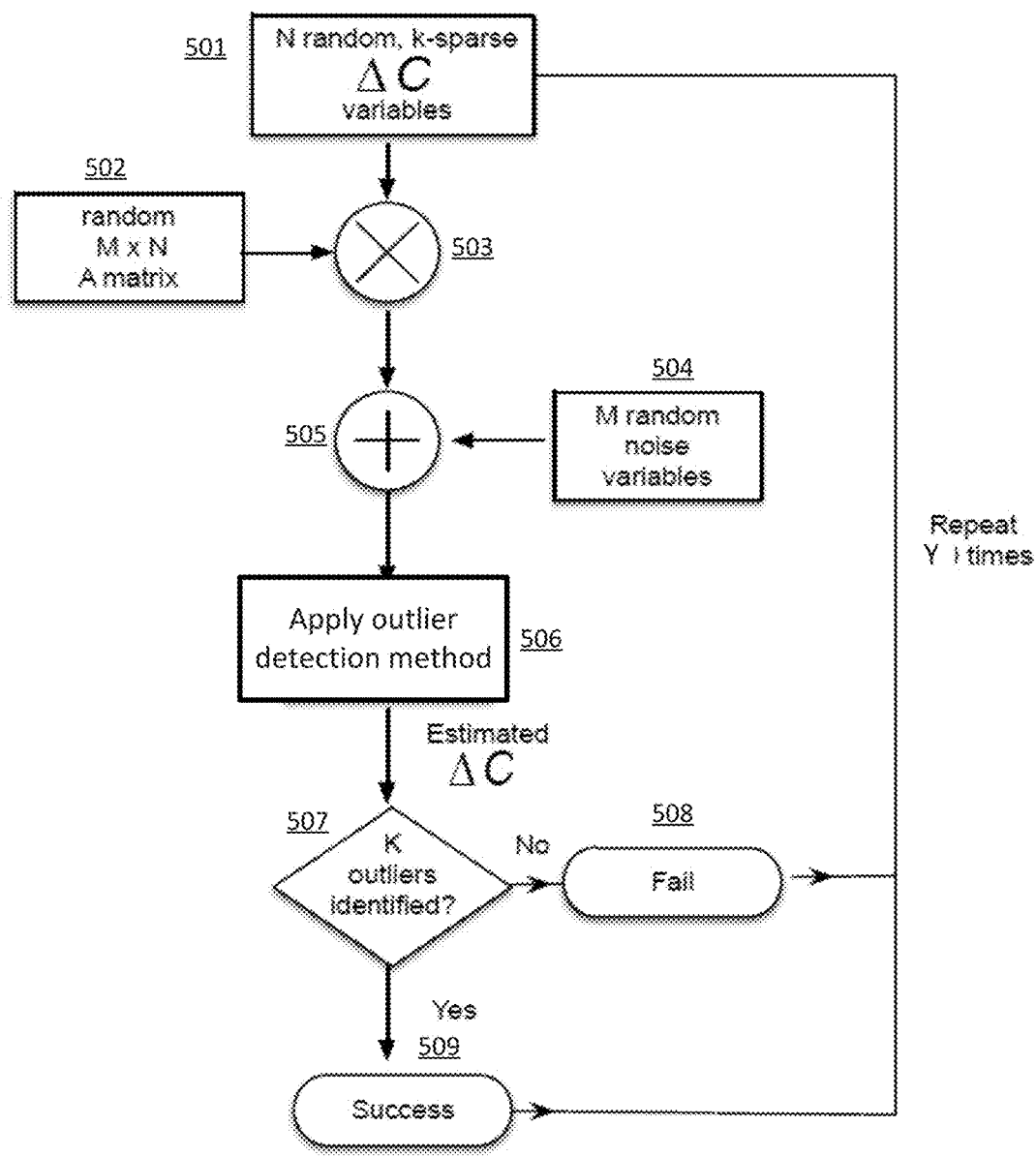
FIG. 5 is a flowchart that illustrates a simulation method utilized to verify the outlier behavior detection method, according to an example embodiment of the present invention.

FIG. 5 depicts an example embodiment of a simulation method utilized to verify the outlier behavior detection method. In step 501, a column vector (i.e., ΔC) with N-random variables, i.e., an artificially generated set of electrodes with outlier behavior, is generated. Further, in an example embodiment, of the N-random variables generated, there are K-sparse ΔC variables, which are the only variables among the N-random variables which are non-zero. In step 502, an M×N matrix (e.g., matrix A) is generated with a random distribution of 1s and 0s, where M corresponds to the number of measurements. In step 503, the product of the matrix (e.g., matrix A) generated in step 502 and the column vector generated in step 501 is determined. In step 504, a matrix containing M random noise variables is generated. In an example embodiment, each row of the matrix contains at least one random noise variable. In step 505, the sum of the M×N matrix generated in step 503 and the matrix containing the M random noise variables generated in step 504 is determined. In step 506, the outlier detection method of the present invention is applied to the matrix generated in step 505 in order to estimate the ΔC variables. In step 507, it is determined whether the estimated ΔC variables correctly identify the K outliers generated in step 501. If the estimated ΔC variables correctly identify the K outliers generated in step 501 then, in step 509, the simulation is marked as a success. However, if the estimated ΔC variables do not correctly identify the K outliers generated in step 501 then, in step 508, the simulation is marked as a failure. In an example embodiment, the simulation is repeated Y times, and, after Y simulations, the success rate of the outlier detection method can be determined.

FIG. 6A shows the probability of success for different outlier occurrences in 20 electrodes using the simulation method of FIG. 5 for 100 trials. Specifically, FIG. 6A shows the probability of success of the outlier detection method for an electrode array with 1, 2, 3, 4, and 5 outliers, respectively.

FIG. 6B shows the probability of success for different outlier occurrences in 50 electrodes using the simulation method of FIG. 5 for 500 trials. Specifically, FIG. 6B shows the probability of success of the outlier detection method for an electrode array with 1, 2, 3, 4, and 5 outliers, respectively.

Figure 6C:
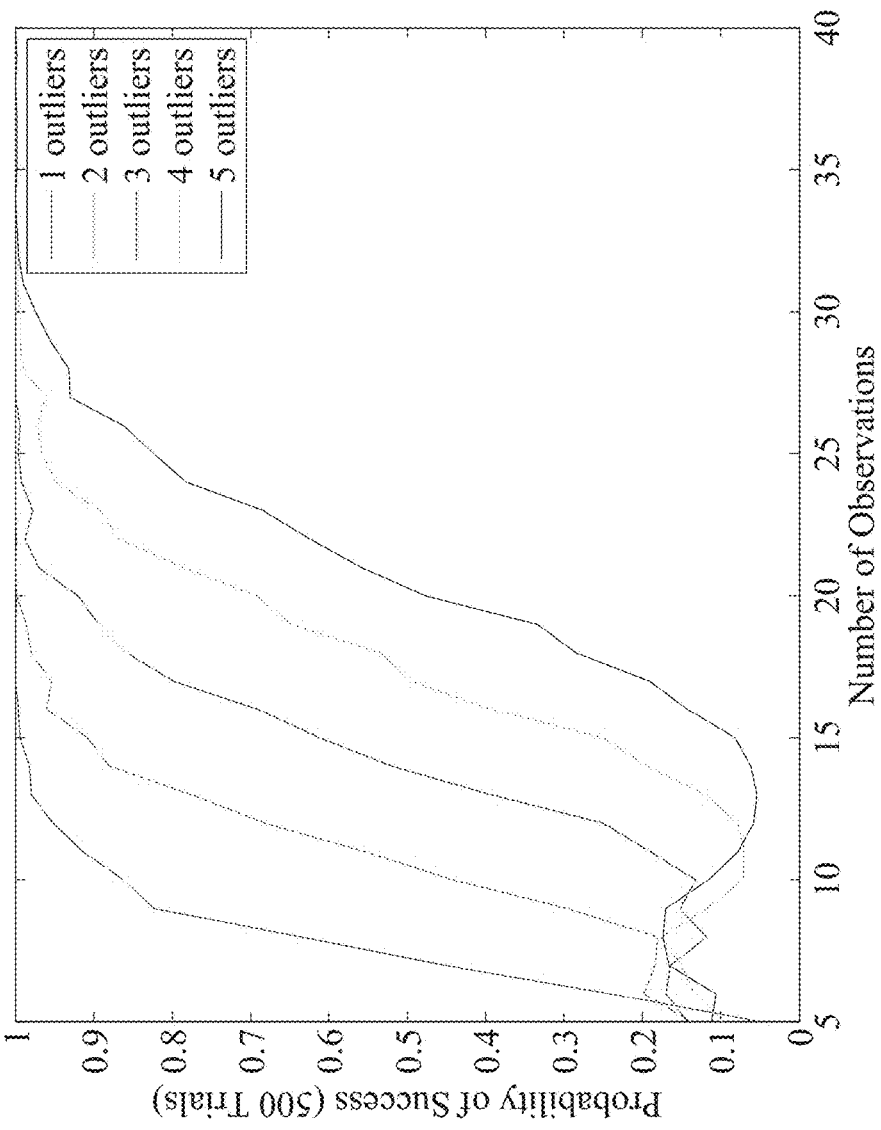
FIG. 6C depicts the probability of success for different outlier occurrences in 100 electrodes using the simulation method of FIG. 5 for 500 trials, according to an example embodiment of the present invention.

FIG. 6C shows the probability of success for different outlier occurrences in 100 electrodes using the simulation method of FIG. 5 for 500 trials. Specifically, FIG. 6C shows the probability of success of the outlier detection method for an electrode array with 1, 2, 3, 4, and 5 outliers, respectively.

FIG. 6D depicts the probability of success for different outlier occurrences in 200 electrodes using the simulation method of FIG. 5 for 100 trials. Specifically, FIG. 6D shows the probability of success of the outlier detection method for an electrode array with 1, 2, 3, 4, and 5 outliers, respectively.

FIG. 6E shows the probability of success for different measurement noise variances for 5 outliers in 100 electrodes using the simulation method of FIG. 5 for 500 trials. Specifically, FIG. 6E depicts the probability of success of the outlier detection method for a noise variance of 0.05 sigma, 0.15 sigma, 0.75 sigma, 0.105 sigma, and 0.45 sigma, respectively.

Figure 6F:
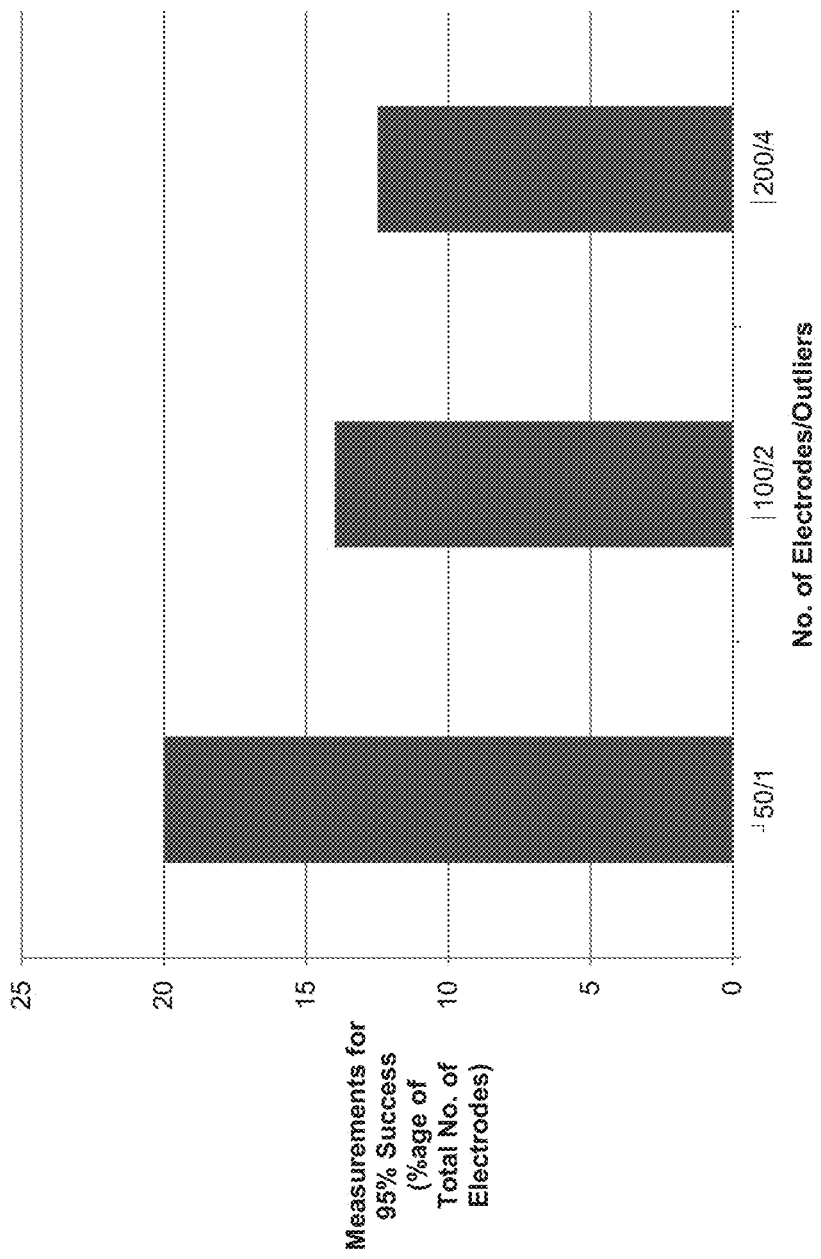
FIG. 6F depicts the number of measurements required for various electrode/outlier combinations to achieve a 95% success rate with the simulation method of FIG. 5, according to an example embodiment of the present invention.

FIG. 6F shows the number of measurements required for various electrode/outlier combinations to achieve a 95% success rate with the simulation method of FIG. 5. As shown in FIG. 6F, for an electrode array of 50 electrodes with 1 outlier, 20 measurements are enough. Further, for an electrode array of 100 electrodes with 2 outliers, approximately 14 measurements are required. Similarly, for an electrode array of 200 electrodes with 4 outliers, approximately 13 measurements are required.

The foregoing systems and methods can be used on any electrode array irrespective of the specific substrate (e.g., glass substrate, silicon, etc.), electrode material (e.g., ITO, platinum, etc.) and redox couples (e.g., cyanide; methyl-1, 4-hydroquinone/methyl-1, 4-benzoquinone; etc.). In addition, the parameters of interest can either be a small or large signal. Further, the parameters of interest can be time-varying or time invariant. The foregoing systems and methods can also be applied to single photon avalanche diodes and battery cell testing.

The above description is intended to be illustrative, and not restrictive. Those skilled in the art can appreciate from the foregoing description that the present invention may be implemented in a variety of forms, and that the various embodiments can be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and the claims below. Further, steps illustrated in the flowcharts may be omitted and/or certain step sequences may be altered, and, in certain instances multiple illustrated steps may be simultaneously performed.

What is claimed is:

1. A system for monitoring and regulating an electrode array that includes n electrodes, the system comprising:
    a measuring circuit;
    at least one scan chain that each includes a respective plurality of memory elements, wherein each of the memory elements corresponds to a respective one of the n electrodes in the electrode array; and
    a processing circuit, wherein the processing circuit is configured to:
    for each of m iterations:
    generate a respective random sequence of 1s and 0s that each corresponds to a respective one of the electrodes in the electrode array so that all of the n electrodes in the electrode array is assigned either one of the 1s or one of the 0s, the respective random sequence varying between different ones of the m iterations;
    supply the random sequence to the at least one scan chain; and
    trigger the measuring circuit to perform a measurement by (a) setting, according to the random sequence in the at least one scan chain, each of the electrodes that has been assigned one of the 1s as enabled and setting each of the electrodes that has been assigned one of the 0s as disabled, (b) supplying a voltage to all of the enabled ones of the electrodes and not the disabled ones of the electrodes, such that, in different ones of the iterations, different subsets of the n electrodes are supplied the voltage, and (c) detecting a respective value of an electrical feature produced by all of the enabled electrodes of the respective iteration as a whole as a result of respective unknown values of the electrical feature exhibited by each of the enabled electrodes;

solve for x in Ax=b, wherein:
A is a m×n matrix populated with the 1s and 0s of the random sequences of the m iterations, so that each position of the matrix A corresponds to a respective one of the n electrodes during a respective one of them iterations and is populated with a 1 if the respective electrode to which the respective position corresponds was enabled during the respective iteration to which the respective position corresponds and is populated with a 0 if the respective electrode to which the respective position corresponds was disabled during the respective iteration to which the respective position corresponds;
x is a column vector of n positions, a respective value for each of which is the respective unknown value of the electrical feature exhibited specifically by a respective one of the n electrodes of the electrode array when the respective electrode is enabled;
b is a column vector of m positions that each corresponds to a respective one of the iterations and a respective value of each of which is the respective detected value that had been detected in the respective iteration to which the respective position corresponds;
the solving for x includes determining a plurality of solutions; and
each of the solutions is a respective set of values that is each assigned to a respective one of the n positions of x, by which set of values Ax=b is true;
determine for each of the solutions, a respective sum of all of the values of the respective solution of column vector x in absolute form;
from all of the determined solutions, select whichever one of the solutions has a lowest of the determined sums;
identify one or more faulty electrodes based on the selected solution; and
regulate the electrodes of the electrode array based on the identification of the one or more faulty electrodes;
wherein m is a respective number more than 1 and n is a respective number more than 1.

2. The system of claim 1, wherein the electrode array is implemented in one of a (1) glass slide and a (2) complementary metal-oxide semiconductor (CMOS) chip.

3. The system of claim 1, wherein the electrode array is implemented on a combination of a glass slide and a complementary metal-oxide semiconductor (CMOS) chip.

4. The system of claim 1, wherein the at least one scan chain includes a shift register.

5. The system of claim 1, wherein the measuring circuit and the at least one scan chain interface with the electrodes of the electrode array through at least one of a (1) decoder circuit and (2) multiplexer.

6. The system of claim 1, wherein the scan chain is implemented with (1) capacitors or (2) flip-flops.

7. The system of claim 1, further comprising:
an electrical line; and
a switching circuit via which the electrodes are individually coupleable to the electrical line;
wherein:
the supplying of the voltage to all of the enabled ones of the electrodes includes coupling, by the switching circuit, the enabled ones of the electrodes to the electrical line;
the detecting of the respective value includes a sensor sensing an electrical parameter produced over the electrical line by the coupled electrodes, the respective value being a value of the sensed electrical parameter;

m is less than n;
the identification of the one or more faulty electrodes includes identifying those of the electrodes that exhibit outlier electrical behavior based on the respective values of the electrical feature assigned by the selected solution to the respective electrodes of the electrode array; and
the selected solution is selected so that the values of the selected solution can result in all of the respective detected values of all of the m iterations.

8. The system of claim 7, wherein subsets of the electrodes that are coupled to the electrical line differ between at least two of the iterations.

9. The system of claim 7, wherein the solving for x is performed by the determining of the plurality of solutions being performed such that the respective sets of values of each of the solutions is a respective set of electrical values ascribed to respective ones of the individual electrodes that can result in all of the respective values of each of the m iterations.

10. The system of claim 7, wherein:
each row of matrices A and b corresponds to a respective one of the iterations; and
each column of matrix A corresponds to a respective one of the electrodes in the array.

11. The system of claim 10, wherein each value of each solution of column vector x represents a respective contribution of a respective one of the electrodes towards the values of the sensed electrical parameter produced over the electrical line during the iterations.

12. A method for monitoring and regulating an electrode array that includes n electrodes, the method comprising:
for each of m iterations:
generating, with a processor, a respective random sequence of 1s and 0s that each corresponds to a respective one of the electrodes in the electrode array so that all of the n electrodes in the electrode array is assigned either one of the 1s or one of the 0s, the respective random sequence varying between different ones of the m iterations;
enabling each of the electrodes that has been assigned one of the 1s according to the generated random sequence of the respective iteration, each of the electrodes that has been assigned one of the 0s being disabled;
supplying, with a measurement line, a voltage to all of the enabled ones of the electrodes and not the disabled ones of the electrodes, such that, in different ones of the iterations, different subsets of then electrodes are supplied the voltage; and
detecting, with the measurement line, a respective value of an electrical feature produced by all of the enabled electrodes of the respective iteration as a whole as a result of respective unknown values of the electrical feature exhibited by each of the enabled electrodes;
solving, by the processor, for x in Ax=b, wherein:
A is a m×n matrix populated with the 1s and 0s of the random sequences of the m iterations, so that each position of the matrix A corresponds to a respective one of the n electrodes during a respective one of them iterations and is populated with a 1 if the respective electrode to which the respective position corresponds was enabled during the respective iteration to which the respective position corresponds and is populated with a 0 if the respective electrode to which the respective position corresponds was disabled during the respective iteration to which the respective position corresponds;

x is a column vector of n positions, a respective value for each of which is the respective unknown value of the electrical feature exhibited specifically by a respective one of the n electrodes of the electrode array when the respective electrode is enabled;

b is a column vector of m positions that each corresponds to a respective one of the iterations and a respective value of each of which is the respective detected value that had been detected in the respective iteration to which the respective position corresponds;

the solving for x includes determining a plurality of solutions; and each of the solutions is a respective set of values that is each assigned to a respective one of the n positions of x, by which set of values Ax=b is true;

determining, by the processor, for each of the solutions, a respective sum of all of the values of the respective solution of column vector x in absolute form;

from all of the determined solutions, selecting, with the processor, whichever one of the solutions has a lowest of the determined sums;

identifying, by the processor, one or more faulty electrodes based on the selected solution; and regulating, by the processor, the electrodes of the electrode array based on the identification of the one or more faulty electrodes;

wherein m is a respective number more than 1 and n is a respective number more than 1.

13. The method of claim 12, wherein the regulating includes (1) adjusting the voltage being applied to the one or more faulty electrodes or (2) disabling the one or more faulty electrodes.

14. The method of claim 12, further comprising:

dividing, by the processor, the electrode array into at least two sub-arrays;

determining, by the processor, which sub-array of the at least two sub-arrays includes the one or more faulty electrodes; and reapplying, by the processor, the steps of claim 6 to the at least one sub-array determined as including one or more faulty electrodes.

15. The method of claim 12, wherein the one or more faulty electrodes is determined from those of the electrodes to which non-zero values of the selected solution of x correspond.

16. The method of claim 12, wherein m<n.

17. The method of claim 12, wherein in each of the iterations, a first subset of the respective random sequence of 1s and 0s is supplied to a first scan chain and a second subset of the respective random sequence, which differs from the first subset, is supplied to a second scan chain, and the enabling is performed based on the values in the scan chain.

18. The method of claim 12, wherein the one or more at least one faulty electrodes have current-voltage characteristics that deviate by a predefined threshold amount from a mean of the current-voltage characteristics of a general population of electrodes in the electrode array.

19. A non-transitory computer readable medium containing program instructions that are executable by one or more processors of a computer system and that, when executed by one or more processors, causes the one or more processors to perform a method for monitoring and regulating an electrode array that includes n electrodes, the method comprising:

for each of m iterations:

generating a respective random sequence of 1s and 0s that each corresponds to a respective one of the electrodes in the electrode array so that all of the n electrodes in the electrode array is assigned either one of the 1s or one of the 0s, the respective random sequence varying between different ones of the m iterations; and triggering a measuring circuit to perform a measurement by (a) setting each of the electrodes that has been assigned one of the 1s as enabled and setting each of the electrodes that has been assigned one of the 0s as disabled, (b) supplying a voltage to all of the enabled ones of the electrodes and not the disabled ones of the electrodes, such that, in different ones of the iterations, different subsets of then electrodes are supplied the voltage, and (c) detecting a respective value of an electrical feature produced by all of the enabled electrodes of the respective iteration as a whole as a result of respective unknown values of the electrical feature exhibited by each of the enabled electrodes;

solving for x in Ax=b, wherein:

A is a m×n matrix populated with the 1s and 0s of the random sequences of the m iterations, so that each position of the matrix A corresponds to a respective one of the n electrodes during a respective one of them iterations and is populated with a 1 if the respective electrode to which the respective position corresponds was enabled during the respective iteration to which the respective position corresponds and is populated with a 0 if the respective electrode to which the respective position corresponds was disabled during the respective iteration to which the respective position corresponds;

x is a column vector of n positions, a respective value for each of which is the respective unknown value of the electrical feature exhibited specifically by a respective one of the n electrodes of the electrode array when the respective electrode is enabled;

b is a column vector of m positions that each corresponds to a respective one of the iterations and a respective value of each of which is the respective detected value that had been detected in the respective iteration to which the respective position corresponds;

the solving for x includes determining a plurality of solutions; and each of the solutions is a respective set of values that is each assigned to a respective one of the n positions of x, by which set of values Ax=b is true;

determining, for each of the solutions, a respective sum of all of the values of the respective solution of column vector x in absolute form;

from all of the determined solutions, selecting whichever one of the solutions has a lowest of the determined sums;

identifying one or more faulty electrodes based on the selected solution; and regulating the electrodes of the electrode array based on the identification of the one or more faulty electrodes;

wherein m is a respective number more than 1 and n is a respective number more than 1.

20. The non-transitory computer readable medium of claim 19, wherein the regulating includes (1) adjusting the voltage being applied to the one or more faulty electrodes or (2) disabling the one or more faulty electrodes.

21. The non-transitory computer readable medium of claim 19, wherein the method further comprises:

dividing the electrode array into at least two sub-arrays;

determining which sub-array of the at least two sub-arrays includes the one or more faulty electrodes; and reapplying the steps of claim 19 to the at least one sub-array determined as including the one or more faulty electrodes.

22. The non-transitory computer readable medium of claim 19, wherein the one or more faulty electrodes is determined from those of the electrodes to which non-zero values of the selected solution of x correspond.

23. The non-transitory computer readable medium of claim 19, wherein m <n.

24. The non-transitory computer readable medium of claim 19, wherein in each of the iterations, a first subset of the respective random sequence of 1s and 0s is supplied to a first scan chain and a second subset of the respective random sequence, which differs from the first subset, is supplied to a second scan chain, and the setting of electrodes to be enabled is performed based on the values in the scan chains.

25. The non-transitory computer readable medium of claim 19, wherein the one or more at least one faulty electrodes have current-voltage characteristics that deviate by a predefined threshold amount deviate from a mean of the current-voltage characteristics of a general population of electrodes in the electrode array.

\* \* \* \* \*